United States Patent [19]

Masui et al.

[11] Patent Number: 5,146,164
[45] Date of Patent: Sep. 8, 1992

[54] EDDY CURRENT FLAW DETECTION APPARATUS EMPLOYING A RESONANCE CIRCUIT

[75] Inventors: Tsutomu Masui; Kazumasa Hori, both of Sakai; Akio Ueno, Ikeda, all of Japan

[73] Assignee: Mitsubishi Materials Corporation, Japan

[21] Appl. No.: 725,553

[22] Filed: Jul. 3, 1991

[30] Foreign Application Priority Data

Jul. 4, 1990 [JP] Japan .................................. 2-176972

[51] Int. Cl.⁵ ...................... G01N 27/82; G01R 33/12
[52] U.S. Cl. .................................. 324/233; 324/237; 324/238
[58] Field of Search .............. 324/225, 233, 238, 239, 324/241, 242, 243, 237, 240

[56] References Cited

U.S. PATENT DOCUMENTS 4,107,605 8/1978 Hudgell .............................. 324/238

FOREIGN PATENT DOCUMENTS 0107844 5/1984 European Pat. Off. .
0315887 5/1989 European Pat. Off. .

OTHER PUBLICATIONS

Patent Abstracts of Japan, vol. 11, No. 156 (P-578)(2603), May 21, 1987, JP-A-61-292548, (Mitsubishi Metal Corp.), Dec. 23, 1986.

Primary Examiner—Walter E. Snow
Attorney, Agent, or Firm—Scully, Scott, Murphy & Presser

[57] ABSTRACT

An eddy current flaw detection apparatus, having: a pair of detecting coils disposed in a separated manner along a transit path of a conductor and coaxial with the conductor, magnetic fields generated by said detecting coils being in anti-phase; an alternating current bridge circuit, two sides of a bridge of which are comprising the detecting coils, and which, when a relative change occurs in inductances of the detecting coils and equilibrium of the bridge is thus disturbed, outputs an abnormality detection signal; a pair of resonance coils, which are disposed between the detecting coils, and coaxial with the detecting coils, and magnetic fields of which are in phase, and which are so set that in a state in which the bridge is in equilibrium, induction currents generated by said resonance coils cancel each other out; and a capacity circuit for the purpose of bringing oscillation frequencies of the detecting coils into resonance, which is connected to the resonance coils.

5 Claims, 4 Drawing Sheets

EDDY CURRENT FLAW DETECTION APPARATUS EMPLOYING A RESONANCE CIRCUIT

BACKGROUND OF THE INVENTION

1. Field of the Invention

The present invention relates to an eddy current flaw detection apparatus for the detection of flaws or contaminating foreign material in metal members.

2. Prior Art

In the production processes of copper wiring or the like, if there is contaminating foreign matter, such as a piece of iron or the like, within the copper wiring material, or if there is a flaw in this material, this can result in disconnection during the wire drawing process. For this reason, it is necessary to determine whether foreign matter or flaws or the like are present before the wire drawing process.

Conventionally, in this type of detection, an eddy current flaw detection apparatus such as that shown in FIGS. 6 to 8 was used. Reference numeral 1 indicates a traveling conductor; detection coils La and Lb, which are coaxial with conductor 1, and do not make contact with conductor 1, are disposed in a separated manner. Detecting coils La and Lb are connected so as to form the two sides of an alternating current bridge circuit, and in the case in which there is no flaw in the conductor 1 which passes through detecting coils La and Lb, the output signal between terminals a and b is so adjusted as to have a zero balance.

In accordance with this apparatus, in the case in which a flaw or foreign matter passes through detecting coils La and Lb, the eddy current within conductor 1 changes, a difference occurs in the inductances of detecting coils La and Lb, and the zero balance is disrupted, so that an output signal is generated between terminals A and B, and it is possible to conduct the detection of flaws or foreign matter based on this signal.

A structure in which the detecting coils La and Lb are connected in a differential manner so that the directions of their magnetic fields are opposed, as shown by the arrows in FIG. 8, is preferable to a structure in which the detecting coils La and Lb are connected in an accumulated manner so that the directions of their magnetic fields are in phase, as shown by the arrows in FIG. 7.

When this type of differential connection is used, if for example, the conductor 1 becomes eccentric within the detecting coils La and Lb, or the composition of conductor 1 changes, and noise signals are generated in detecting coils La and Lb, these noise signals cancel each other out, the noise component of the output signal is reduced and the SN ratio can be increased.

However, in the above described eddy current flaw detection apparatus, the detecting coils La and Lb normally produce opposing magnetic fields, so that these magnetic fields repel each other, and it is difficult for the magnetic fields to penetrate sufficiently into the interior of conductor 1, so that the partial detection sensitivity is reduced. As a result, in cases in which small flaws or small amounts of foreign matter are position near the axial center of the coil, it is difficult to detect them.

SUMMARY OF THE INVENTION

In the consideration of the above, it is an object of the present invention to provide an eddy current flaw detection apparatus capable of detecting small flaws or small amounts of foreign matter at a high abnormality detection sensitivity.

So as to achieve the above described object, the present invention provides an eddy current flow detection apparatus comprising:

an alternating current bridge circuit having a pair of detecting coils disposed in a separated manner along a transit path of a conductor and coaxial with said transit path of the conductor, magnetic fields to be generated by said detecting coils being opposed, and outputs an abnormality detection signal, when a relative change occurs in inductances of said detecting coils and equilibrium of said bridge is thus disturbed;

a pair of resonance coils, which are disposed between said detecting coils, and coaxial with said detecting coils, and magnetic fields of which are in phase, and which are so set that in a state in which said bridge is in equilibrium, induction currents generated by said resonance coils cancel each other; and a capacity circuit connected to said resonance coils so as to form a resonance circuit.

In this eddy current flaw detecting apparatus, in the state in which there are no flaws or foreign matter in the conductor, the induction currents produced in the resonance coils by means of the electromagnetic induction from the detection coils are opposed, and the electric current values thereof are equal, so that these induction currents cancel each other out and resonance does not occur.

On the other hand, in a case in which a flaw or foreign matter is present within a conductor, there is some unevenness within the magnetic fields produced by the detecting coils, so that a difference is generated in the induction current values generated by the resonance coils, and electric current corresponding to this difference flows, and the resonance coils resonate. By means of this, the induction of the detection coils change further and the equilibrium of the alternating current bridge circuit is disrupted, so that it is possible to increase the sensitivity of detection of abnormal signals in comparison with the conventional apparatus.

The other objects and features of this invention will become understood from the following description with reference to the accompanying drawings.

DETAILED DESCRIPTION OF THE PREFERRED EMBODIMENTS

Figure 1:
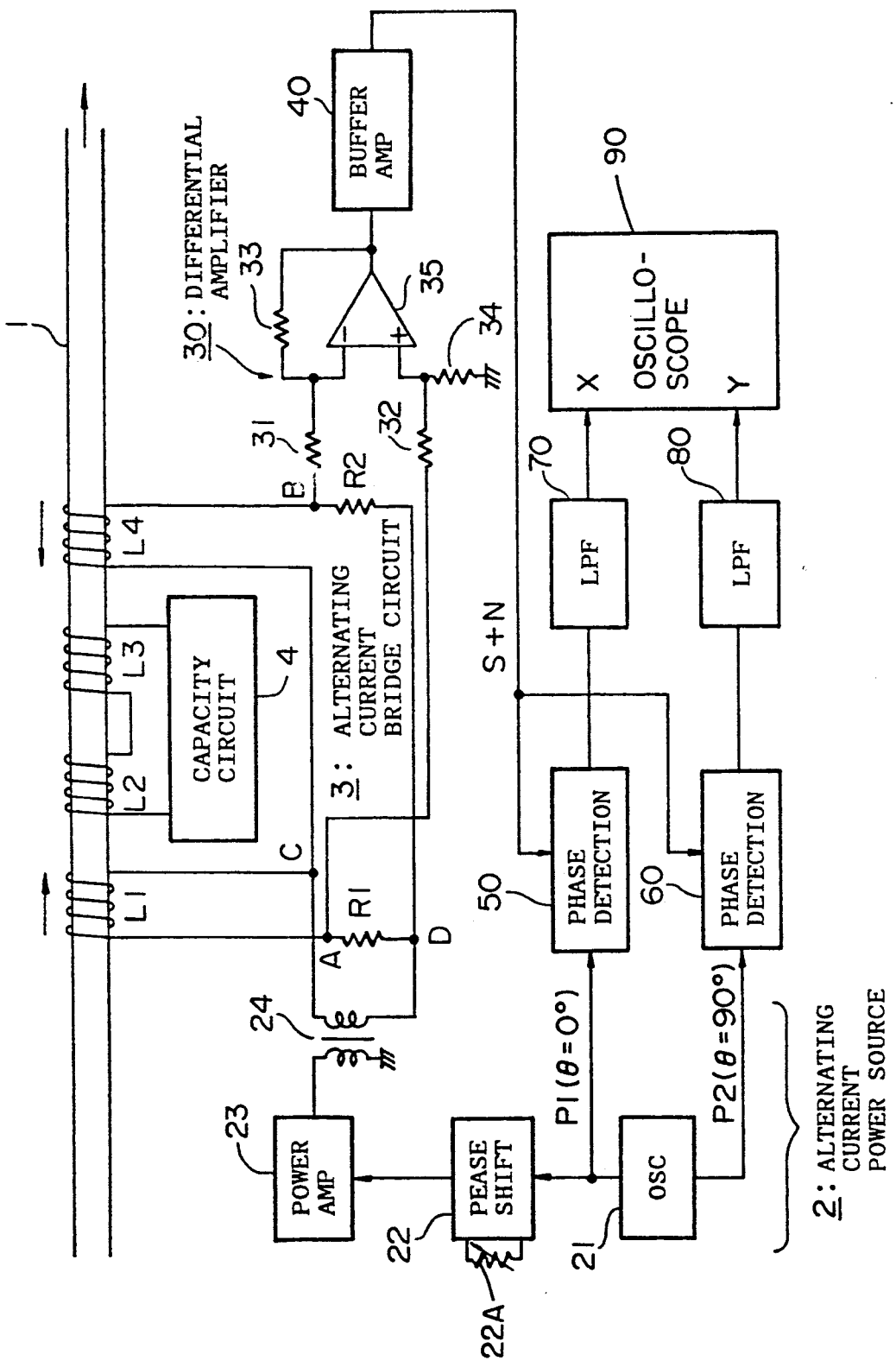
FIG. 1 is a circuit diagram showing an outline of the structure of an eddy current flaw detection apparatus in accordance to the present invention.

FIG. 1 is a circuit diagram showing a preferred embodiment of an eddy current flaw detection apparatus in accordance with the present invention; a detecting coil L1, a resonance coil L2, a resonance coil L3, and a detecting coil L4 are disposed in that order along a conductor 1 which is traveling from a prior process not depicted in the diagram and coaxial with this conductor, and with gaps therebetween in the axial direction thereof.

Detecting coils L1 and L4 are identical to those in the conventional apparatus; they comprise an alternating current bridge circuit 3 together with the two resistors R1 and R2. The detecting coils are connected differentially so that their magnetic fields are opposed. The resistance of R1 and R2 and the inductance of L1 and L4 are determined so that the alternating current bridge circuit 3 is set to a zero balance state and no signal is generated between nodes A and B when there is no abnormality in conductor 1.

On the other hand, resonance coils L2 and L3 are identical; they are connected cumulatively, so that the magnetic fields thereof are in phase. These resonance coils L2 and L3 are connected in series to capacity circuit 4 so as to form a resonance circuit. In a case in which there is no abnormality in conductor 1, the induction current generated by resonance coil L2 by means of the electromagnetic induction of the detecting coil L1, and the induction current generated by resonance coil L3 by means of the electromagnetic induction of the detecting coil L4, are opposed and the electrical current values thereof are equal, so that they are set so as to cancel each other out.

An oscillator 21, a phase shift circuit 22, a power amplifier 23 and a transformer 24 are provided to constitute an alternating current power source 2 which supplies power to alternating current bridge circuit 3. Oscillator 21 generates two periodic signals P1 and P2, which have the same angular frequency $\omega$, and the phase angular of P2 is shifted from that of the P1 by $\pi/2$. Phase shift circuit 22 has an operating member, for example, a volume knob 22a. The output signal P of oscillator 21 is supplied to the phase shift circuit 22 to obtain a signal having a phase which is shifted from the phase of the signal P by the phase shift value corresponding to the operation of the operating member. The phase shift value can be adjusted in the range of 0 through $\pi$ by the operation of the operating member. The output signal of phase shift circuit 22 is amplified in power amplifier 23. The output signal of power amplifier 23 is supplied to one terminal of an input coil of transformer 24. The other terminal of the input coil is grounded. An output coil of transformer 24 is connected between nodes C and D of the alternating current bridge circuit 3.

Resistors 31 through 34 and an operational amplifier 35 are provided to constitute a differential amplifier 30 which amplifies the voltage between nodes A and B of alternating current bridge circuit 3. The output signal of differential amplifier 30 is supplied to a buffer amplifier 40 to obtain a detection signal.

Two phase detection circuits 50 and 60 which have the same function and characteristics are provided. The periodic signal P1 and the detection signal S are respectively supplied to first and second input terminals of phase detection circuits 50. Similarly, the periodic signal P2 and the detection signal S are respectively supplied to first and second input terminals of phase detection circuits 60. Each phase detection circuit detects a same phase component, which is synchronized with the input signal of the first input terminal, from the input signal of the second input terminal. Two low-pass filters 70 and 80 are provided to cut off the higher harmonic components from the output signals of phase detection circuits 70 and 80. The output signals of low-pass filters 70 and 80 are supplied respectively to X-axis and Y-axis input terminals of an oscilloscope 90.

Figure 2:
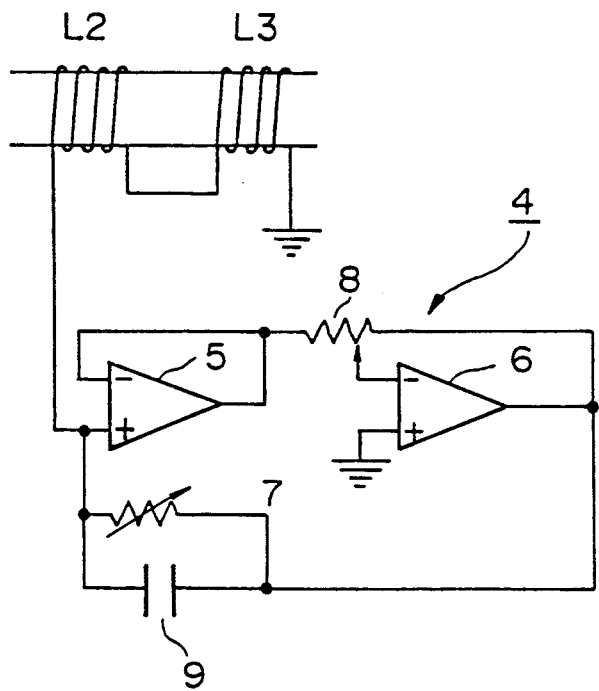
FIG. 2 is a circuit diagram showing an example of a capacity circuit in the same apparatus.

Next, FIG. 2 is a circuit diagram showing a concrete example of the capacity circuit 4; this capacity circuit 4 is primarily comprising two operation amplifiers 5 and 6, variable resisters 7 and 8, and condenser 9. By means of the adjustment of variable resistor 7, it is possible to adjust the resonance frequency of resonance circuit constituted by resonance coils L2 and L3 and capacitance circuit 4, and on the other hand, by means of the adjustment of variable resister 8, it is possible to adjust the resonance Q value of the resonance circuit.

However, the present invention is not limited to the circuitry of FIG. 2; it is also possible to construct the capacity circuit by means of simple condensers or variable capacity condensers, and it is also permissible to alter the circuitry in an appropriate manner, when necessary.

In the eddy current flaw detection apparatus having the above structure, in the case in which there is no flaw or foreign matter in the conductor 1, the induction currents generated by resonance coils L2 and L3, by means of the electromagnetic induction from detecting coils L1 and L4 are in anti-phase, and the current values thereof are equal, so that these induction currents cancel each other out and resonance does not occur.

However, when a flaw or foreign matter of conductor 1 passes the detecting coil L1, the inductance of the detecting coil L1 changes. As a result, an unevenness is generated in the magnetic fields of the detecting coils L1 and L2 so that a difference occurs in the induction currents generated by the resonance coils L2 and L3, and alternating electrical current corresponding to this difference flows, and capacity circuit 4 and resonance coils L2 and L3 resonate. When this occurs, as a result of this, the inductance of detecting coil L1 further increases. As a result, the equilibrium of the alternating current bridge circuit 3 is disrupted, so that a signal is generated between nodes A and B. This signal is amplified through differential amplifier 30 and buffer amplifier 40 to obtain the detection signal. A similar operation occurs when the flaw or foreign matter of conductor 1 passes the detecting coil L4.

Figure 3:
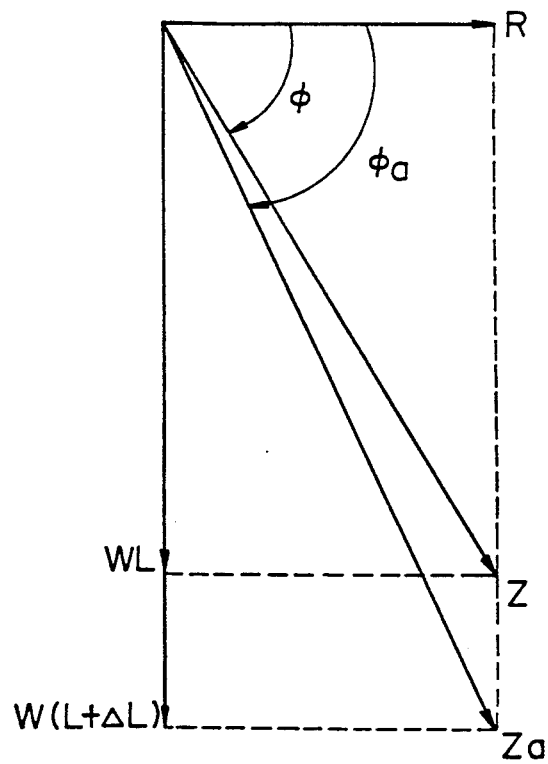
FIGS. 3 and 4 show operations of the same apparatus.

The detection signal includes a detection component S and a noise signal N. The detection component S is generated in response to the change of the impedance of the detecting coil L1 or L4. FIG. 3 shows the change of the impedance of the detecting coil. In the case where the resonance coils L2 and L3 are not used, the impedance Z of the detecting coil is constituted by the resistance R of that and the reactance $\omega L$ of that, wherein the inductance L includes a intrinsic inductance of the detecting coil and an inductance which is generated by the passage of the flaw or foreign matter. In the case where the resonance coils L2 and L3 are used, the inductance of the detecting coil increases from L to $L + \Delta L$ for example. Accordingly, the impedance of the detecting coil changes from Z to Za and the argument of the impedance increases from $\phi = \tan^{-1}(\omega L/R)$ to $\phi a = \tan^{-1}\{\omega(L+\Delta L)/R\}$.

Figure 4:
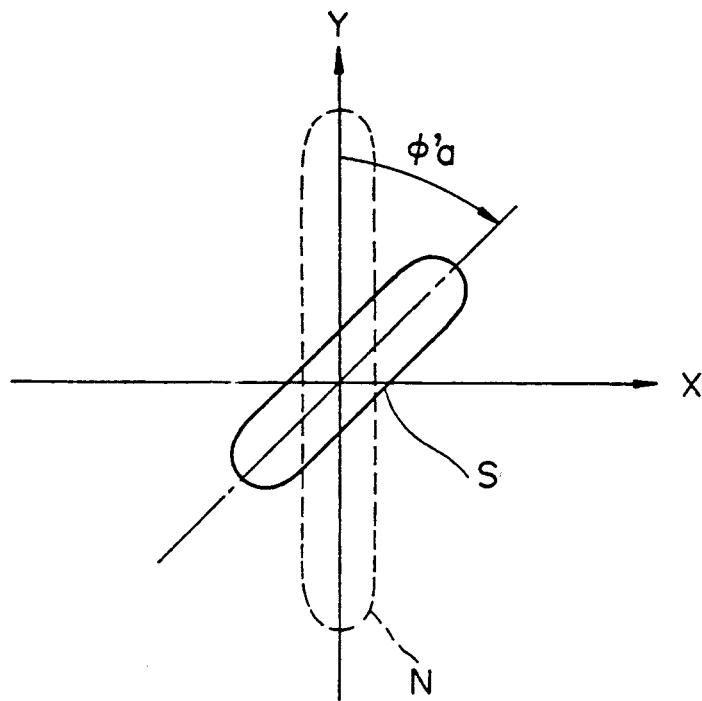

FIG. 4 shows an example of detection component S and noise signal N included in a detection signal. The phase of the detection component S is shifted from that of the noise signal N by angular $\phi a'$ which depends on $\phi a$. The detection signal $S + N$ as thus obtained are supplied to the phase detection circuits 50 and 60. Components synchronized with the periodic signal P1 are detected from the detection signal S+N by the phase detection circuit 50. Similarly, components synchronized with the periodic signal P2 are detected from the phase detection circuit 60. The output signals of the phase detection circuits 50 and 60 are supplied to X-axis and Y-axis input terminals of oscilloscope 90 via low-pass filters 70 and 80. As a result, vectors corresponding to the detection component S and noise signal N are respectively displayed on the oscilloscope in a distinguishable manner, for example, as shown in FIG. 4. Before performing the detection of flaws or foreign matter, an operator adjusts the phase shift value of the phase shift circuit 22 so that the vector of the noise signal S is displayed along X-axis or Y-axis. By this adjustment, the detection component S can be easily distinguished from the noise signal N.

In the preferred embodiment as described above, it is possible to obtain the detection component S of the detection signal with a greater degree of sensitivity than that possessed by the conventional apparatus, and thus it is possible to improve the detection sensitivity with respect to flaws or foreign matter in the conductor 1.

Furthermore, in this apparatus, the amount of separation of the detecting coils L1 and L4 is increased as a result of the provision of resonance coils L2 and L3, so that the canceling out of the magnetic fields of detecting coils L1 and L4 is reduced, and it is thus possible to increase the sensitivity of the apparatus.

In addition, in the apparatus of the present invention, when the material or the dimension of the diameter of conductor 1 change, the inductances of the resonance coils L2 and L3 change ant the resonance frequency changes; however, in the present embodiment, by means of the adjustment of the variable resistor 7 of the capacity circuit 4, it is possible to adjust the resonance frequency of the resonance circuit constituted by the capacity circuit 4 and resonance coils L2 and L3, and it is a simple matter to bring the resonance frequency into agreement with the alternating current power source.

In addition, by means of the adjustment of the variable resistor 8, it is possible to adjust the resonance Q value, so that, it is possible to alter the Q values of the resonance circuit constituted by the resonance coils L2 and L3 and the capacity circuit 4 in the resonance state and to set the abnormality detection sensitivity at an optimun value.

Figure 5:
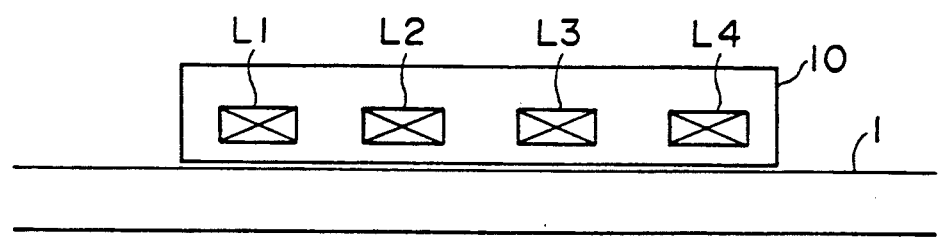
FIG. 5 is an outline diagram showing another preferred embodiment of the present invention.
Figure 6:
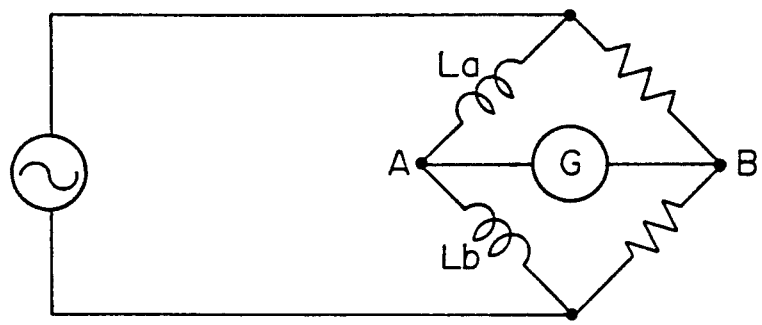
FIG. 6 is an outline diagram showing a conventional eddy current flaw detection apparatus.
Figure 7:
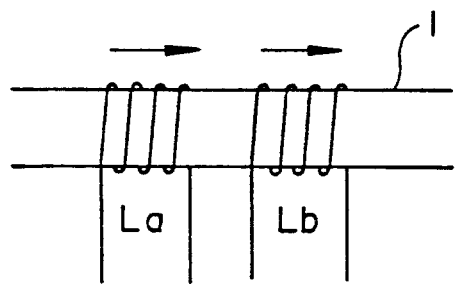
FIGS. 7 and 8 are explanatory diagrams showing the problem points in the conventional apparatus.
Figure 8:
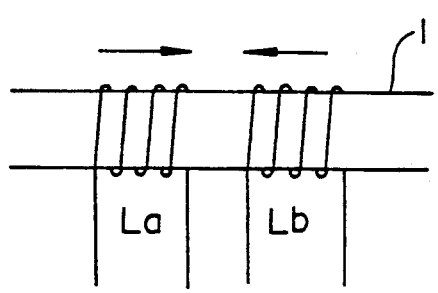

In the present preferred embodiment, the conductor 1 was so disposed as to pass through the coils L1, L2, L3, and L4; however, instead of this, a structure is permissible in which the coils L1, L2, L3, and L4 are enclosed in a casing 10 in a coaxial manner, as shown in FIG. 5, thus forming a measuring element. In this case, the vicinity of the surface of conductor 1 is scanned by means of this measuring element and abnormalities in conductor 1 are thus detected.

What is claimed is:

1. An eddy current flaw detection apparatus comprising:
   an altenating current bridge circuit having a pair of detecting coils disposed in a separated manner along a transit path of a conductor and coaxial with said transit path of the conductor, said detecting coils being connected to form said alternating current bridge circuit in a manner wherein when the same variations of magnetic fields are generated in said detecting coils, the induction voltages generated by said detecting coils cancel each other in said alternating current bridge circuit, and when a relative change occurs in the magnetic fields in said detecting coils, the equilibrium of said alternating current bridge circuit is disturbed, and an abnormality detection signal indicating the relative change is obtained from said alternating current bridge circuit;
   a pair of resonance coils, which are disposed between said detecting coils, and coaxial with said detecting coils such that magnetic fields generated in said detecting coils pass through the adjacent resonance coils, said resonance coils being connected such that when no relative change occurs in the magnetic fields in said detecting coils, said resonance coils generate induction currents due to the corresponding magnetic fields which cancel each other, and when a relative change occurs in the magnetic fields in said detecting coils, said resonance coils generate different induction currents; and
   a capacity circuit connected to said resonance coils to form a resonance circuit.

2. An eddy current flaw detection apparatus in accordance with claim 1, in which said capacity circuit is provided with:
   frequency adjusting means for adjusting resonance frequencies of said resonance circuit.

3. An eddy current flaw detection apparatus in accordance with claim 1, in which said capacity circuit is provided with:
   Q value adjusting means for adjusting resonance Q value of said resonance circuit.

4. An eddy current flaw detection apparatus in accordance with claim 1 further comprising:
   an alternating current power source for generating first and second periodic signals, which have the same angular frequency, and the phase of one is shifted from that of the other by $\pi/2$, one of which is supplied to said alternating current bridge circuit;
   a differential amplifier for amplifying a signal generated between two nodes of said alternating current bridge circuit to obtain a detection signal;
   a first phase detection circuit for detecting an X-axis component signal which is synchronized with said first periodic signal and included in said detection signal;
   a second phase detection circuit for detecting a Y-axis component signal which is synchronized with said second periodic signal and included in said detection signal; and
   a display means for displaying the vector of said detection signal based on said X-axis and Y-axis component signals.

5. An eddy current flaw detection apparatus in accordance with claim 4 further comprising:
   phase adjust means for adjusting the phase of periodic signal supplied to said alternating current bridge circuit.

* * * * *